US011373298B2

(12) United States Patent
Poole

(10) Patent No.: US 11,373,298 B2
(45) Date of Patent: Jun. 28, 2022

(54) APPARATUS AND METHOD FOR TRAINING NEURAL NETWORKS USING SMALL, HETEROGENEOUS COHORTS OF TRAINING DATA

(71) Applicant: CANON MEDICAL SYSTEMS CORPORATION, Otawara (JP)

(72) Inventor: Ian Poole, Edinburgh (GB)

(73) Assignee: CANON MEDICAL SYSTEMS CORPORATION, Otawara (JP)

( * ) Notice: Subject to any disclaimer, the term of this patent is extended or adjusted under 35 U.S.C. 154(b) by 12 days.

(21) Appl. No.: 16/367,955

(22) Filed: Mar. 28, 2019

(65) Prior Publication Data

US 2020/0311911 A1   Oct. 1, 2020

(51) Int. Cl.
*G06T 7/00* (2017.01)
*G06N 3/08* (2006.01)
(Continued)

(52) U.S. Cl.
CPC ............ *G06T 7/0012* (2013.01); *G06N 3/04* (2013.01); *G06N 3/08* (2013.01); *G16H 30/40* (2018.01);
(Continued)

(58) Field of Classification Search
CPC ........ G06N 3/0454; G06N 3/08; G06N 20/00; G06N 3/04; G06N 3/0472; G06N 3/049;
(Continued)

(56) References Cited

U.S. PATENT DOCUMENTS 7,606,779 B2   10/2009 Brinson, Jr.
7,929,739 B2   4/2011 Li
(Continued)

FOREIGN PATENT DOCUMENTS

WO   WO 2018/091486 A1   5/2018

OTHER PUBLICATIONS

Ganin, Y. et al. "Domain-Adversarial Training of Neural Networks" Journal of Machine Learning Research, vol. 17, 2016, 35 Pages.
(Continued)

*Primary Examiner* — Golam Sorowar
(74) *Attorney, Agent, or Firm* — Oblon, McClelland, Maier & Neustadt, L.L.P.

(57) ABSTRACT

A system including processing circuitry configured to train a model for predicting from input data at least one predicted output, wherein the processing circuitry is configured to: receive a plurality of training data sets; receive from a user a selection of a first characteristic including positive and negative samples which are relevant variations significant to prediction of the at least one predicted output; receive from the user a selection of a second characteristic including an irrelevant sample which is a spurious variation irrelevant to the prediction of the predicted output; perform positive supervision of the model using the first characteristic such that the training of the model is sensitive to the positive and negative samples of the first characteristic; and perform negative supervision of the model using the second characteristic such that the training of the model is insensitive to the irrelevant sample of the second characteristic.

19 Claims, 8 Drawing Sheets

(51) Int. Cl.
G06N 3/04 (2006.01)
G16H 50/20 (2018.01)
G16H 30/40 (2018.01)

(52) U.S. Cl.
CPC ... G16H 50/20 (2018.01); *G06T 2207/20081* (2013.01); *G06T 2207/20092* (2013.01)

(58) Field of Classification Search
CPC .................. G06N 3/084; G06N 5/003; G06T 2207/20081; G06T 2207/20084; G06T 2207/10132; G06T 2207/10072; G06T 2207/10081; G06T 2207/10088; G06T 2207/30048; G06T 7/0012; G06T 7/73; G06T 11/60; G06T 2200/04; G06T 2207/10101; G06T 2207/20016; G06T 2207/20024; G06T 2207/30004; G06T 2207/30056; G06T 2207/30101; G06K 9/4628; G06K 9/6256; G06K 2209/051; G06K 9/6215; G06K 9/6255; G06K 9/66; G06K 9/0055; G06K 9/00771; G06K 9/3233; G06K 9/6227; G06K 9/6261; G06K 9/6267; G06K 9/6289
See application file for complete search history.

(56) References Cited

U.S. PATENT DOCUMENTS

| | | | | |
|---|---|---|---|---|
| 10,209,974 | B1* | 2/2019 | Patton | G06N 20/00 |
| 2008/0177680 | A1* | 7/2008 | Laxman | G06K 9/6269 |
| | | | | 706/12 |
| 2012/0197826 | A1* | 8/2012 | Mineno | G06N 20/00 |
| | | | | 706/12 |
| 2015/0043772 | A1 | 2/2015 | Poole et al. | |
| 2016/0093048 | A1* | 3/2016 | Cheng | G06K 9/6289 |
| | | | | 382/131 |
| 2016/0174902 | A1* | 6/2016 | Georgescu | G06T 7/0012 |
| | | | | 600/408 |
| 2017/0011281 | A1 | 1/2017 | Dijkman et al. | |
| 2017/0249534 | A1* | 8/2017 | Townsend | G06N 3/0454 |
| 2017/0270674 | A1* | 9/2017 | Shrivastava | G06K 9/6256 |
| 2018/0240551 | A1* | 8/2018 | Perrey | G16H 50/20 |
| 2018/0307946 | A1* | 10/2018 | Kuroda | G06K 9/6259 |
| 2019/0005547 | A1* | 1/2019 | Tan | G06F 16/435 |
| 2019/0065905 | A1* | 2/2019 | Rephaeli | G06K 9/6256 |
| 2019/0286620 | A1* | 9/2019 | Al-Haimi | G06N 3/0454 |
| 2019/0325861 | A1* | 10/2019 | Singh | G10L 15/16 |
| 2019/0362233 | A1* | 11/2019 | Aizawa | G06N 3/08 |

OTHER PUBLICATIONS

Ben-David, S. et al. "Analysis of Representations for Domain Adaptation" Advances in Neural Information Processing Systems, vol. 19, 2017, 8 Pages.

Kamnitsas, K. et al. "Unsupervised domain adaptation in brain lesion segmentation with adversarial networks" Lecture Notes in Computer Science, 2016, 14 Pages.

Moeskops, P. et al. "Deep Learning for Multi-Task Medical Image Segmentation in Multiple Modalities" Medical Image Computing and Computer-Assisted Intervention, vol. 2, 2016, 9 Pages.

Graves, A. et al. "Automated Curriculum Learning for Neural Networks" Google DeepMind, 2017, 10 Pages.

Dou, Q. et al. "3D Deeply Supervised Network for Automatic Liver Segmentation from CT Volumes" https://arxiv.org/pdf/1607.00582.pdf, vol. 1, 2016, 8 Pages.

Dabbah, M.A. et al. "Detection and location of 127 anatomical landmarks in diverse CT datasets" SPIE Medical Imaging, vol. 9034, 2014, 12 Pages.

Quinlan, J.R. "Chapter 3, Unknown Attribute Values" C4.5 : Programs for Machine Learning, 1993, 8 Pages.

Extended European Search Report dated Aug. 28, 2020 in European Patent Application No. 201550845, 7 pages.

\* cited by examiner

APPARATUS AND METHOD FOR TRAINING NEURAL NETWORKS USING SMALL, HETEROGENEOUS COHORTS OF TRAINING DATA

FIELD

Embodiments described herein relate generally to an apparatus and method for training models, for example training neural networks using small, heterogeneous cohorts of training data.

BACKGROUND

Medical image data may be obtained by using a medical imaging scanner to scan at least part of the body of a patient or other subject. For example, a computed tomography (CT) scanner, magnetic resonance (MR) scanner, or scanner in any other medical imaging modality may be used. Medical image data may be two-dimensional (planar) or three-dimensional (volumetric). A set of medical image data may be representative of, or may be processed to provide, a medical image, for example a medical image for display.

It is common to refer to the processing of medical images and the processing of medical image data interchangeably. For example, one may refer to the segmentation of a medical image or to edge detection in a medical image, when in practice the operations are performed on medical image data that is representative of the medical image. In the description below, references to processing of medical images may be considered to include the processing of corresponding medical image data.

It is known to analyze medical images to obtain medically relevant information. For example, medical images may be analyzed to obtain a segmentation of one or more organs that are represented. Medical images may be analyzed to detect pathological regions. Medical images may be analyzed to predict long-term patient outcomes.

In many cases, medical images are analyzed manually by a clinician, for example a radiologist. In some cases, medical images may be analyzed automatically.

A system may be trained to recognize patterns in image data, for example medical image data. Pattern recognition may comprise for example, object classification from images. Pattern recognition may comprise any suitable regression, detection, or other pattern recognition process.

The system may be trained using sets of image data, which may be described as training data. The training data may comprise sets of image data that have already been analyzed manually to obtain a desired output. For example, in a case in which the system is to be trained to perform a segmentation, each training data set may comprise a manual segmentation of a corresponding image. The manual segmentation may be used as ground truth.

In general, traditional approaches to pattern recognition use relatively small quantities of training data to train a system to perform pattern recognition. Such traditional approaches may generally involve substantial expertise from a domain expert to normalize data and to devise meaningful features from the training data. The traditional pattern recognition methodology may be cumbersome, involving fixed normalization and feature extraction algorithms which may not be an ideal fit. In a traditional approach, these cumbersome algorithms are implemented in product, which results in a complex and computationally costly delivered solution.

FIG. 1 is a flow chart illustrating in overview a method of training a classifier using a traditional pattern recognition approach. A training system receives a plurality of sets of primary training data 10. In the example of FIG. 1, each of the sets of primary training data 10 comprises a respective set of medical image data that is representative of a respective medical image.

Each of the sets of primary training data has already been classified. For example, the sets of primary training data may have been classified manually by one or more clinicians. Based on the classification, a respective label is associated with each set of primary training data. The label may be referred to as a primary ground truth label or primary GT label. The labels may relate to any characteristic of interest. For example, the labels may indicate the presence or absence of a pathology.

At stage 12, a domain expert 2 (illustrated by a picture of Rodin's sculpture The Thinker) performs a normalization of the primary training data to remove irrelevant variations. For example, the domain expert 2 may rotate at least some of the images such that all of the images have substantially the same orientation. The domain expert 2 may normalize the images to remove an effect of lighting conditions, for example normalizing the images such that the images have similar average intensity or range of intensities. The normalization step of stage 12 is particularly concerned with removing variations (which may be described as artifacts) of data acquisition, for example spatial scale, intensity bias, or shading (intensity change across the image).

At stage 14, the domain expert 2 selects a plurality of features to be computed from the medical image data sets (which may be described as raw data). The features are designed to capture significant variations, which are relevant to the classifier that is being trained. The domain expert 2 selects features based on the expert's domain experience. For example, the domain expert 2 may know from experience which features are likely to correlate with a desired classification.

For example, the domain expert 2 may select a set of features comprising one or more intensity features, for example, statistical moments (for example mean and/or standard deviation) of intensity or intensity gradients. Often, some automatic segmentation (e.g. by thresholding) is involved. The set of features may comprise features of the segmented object, for example area, perimeter, circularity and/or convex hull area (or their 3D analogues).

The training system computes values for each of the selected features in each of the training data sets.

At stage 16, the training system receives the values for the computed features obtained at stage 14. The training system receives the primary ground truth labels 18 for each of the sets of primary training data 10. The training system trains a classifier to predict class labels based on computed values for the selected features.

The approach shown in FIG. 1 uses a large amount of input from a domain expert 2. The domain expert 2 performs the normalization and selects the features to be used in training the classifier.

An alternative approach to automated pattern recognition may be provided by deep learning. In general, deep learning neural network approaches avoid the need for explicit normalization or feature measurement. Deep learning neural network approaches have been hugely successful in recent years. However, deep learning neural network approaches typically require large amounts of training data if they are to generalize well.

FIG. 2 is a flow chart illustrating in overview a method of training a classifier using a deep learning approach. A large quantity of primary raw training data 20 is provided to a neural network 22. The primary raw training data 20 comprises a large number of medical image data sets. The primary raw training data 20 is provided to the neural network 22 without the primary raw training data 20 having been normalized or features having been extracted from the primary raw training data 20.

The neural network 22 also receives primary ground truth labels 24 for each of the sets of primary raw training data 20. The primary ground truth labels 24 have been obtained by prior classification of each of the medical image data sets, for example manual classification by a clinician.

The system trains the neural network 22 to perform a prediction directly from the medical image data sets (which may be described as raw data). The neural network 22 learns to classify data to predict labels for medical image data sets without explicit normalization or feature measurement.

Deep learning has been demonstrated to work well when plentiful tuning data is available. However, it typically works less well when training data is in short supply.

BRIEF DESCRIPTION OF THE DRAWINGS

Embodiments are now described, by way of non-limiting example, and are illustrated in the following figures, in which.

DETAILED DESCRIPTION

Certain embodiments provide a system comprising processing circuitry configured to perform a training method to train a model for predicting from input data at least one predicted output, the training method comprising: receiving a plurality of training data sets; receiving from a user an identification of a first characteristic of the training data sets as a positive characteristic which is relevant to prediction of the at least one predicted output; receiving from the user an identification of a second characteristic of the training data sets as a negative characteristic which is less relevant or irrelevant to prediction of the at least one predicted output; and training the model, the training of the model comprising: performing supervision of the model using the positive characteristic such that the model is trained to use values for the positive characteristic in the prediction of the at least one predicted output; and performing negative supervision of the model using the negative characteristic.

Certain embodiments provide a training method to train a model to predict from input data at least one predicted output, the input data including image data, the training method comprising: receiving a plurality of training data sets; receiving from a user an identification of a first characteristic of the training data sets as a positive characteristic; receiving from the user an identification of a second characteristic of the training data sets as a negative characteristic; and training the model, the training of the model comprising: performing supervision of the model using values for the positive characteristic such that the model is trained to use values for the positive characteristic in the prediction of the at least one predicted output; and performing supervision of the model using values for the negative characteristic.

Certain embodiments provide a system comprising processing circuitry configured to: receive a target data set; and process the target data set using a trained model to predict at least one predicted output for the target data set, wherein the model is trained using a method comprising: receiving a plurality of training data sets; receiving from a user an identification of a first characteristic of the training data sets as a positive characteristic; receiving from the user an identification of a second characteristic of the training data sets as a negative characteristic; and training the model, the training of the model comprising: performing supervision of the model using values for the positive characteristic such that the model is trained to use values for the positive characteristic in the prediction of the at least one predicted output; and performing supervision of the model using values for the negative characteristic.

Figure 1:
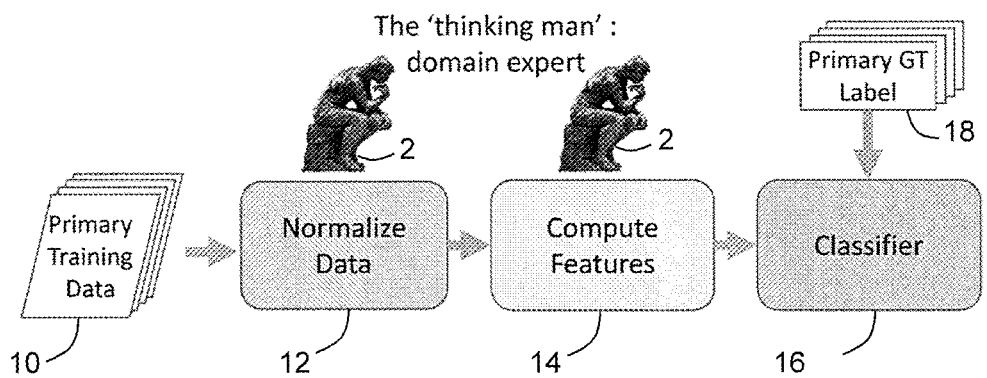
FIG. 1 is a flow chart illustrating in overview a method of training a classifier using a traditional pattern recognition approach.
Figure 2:
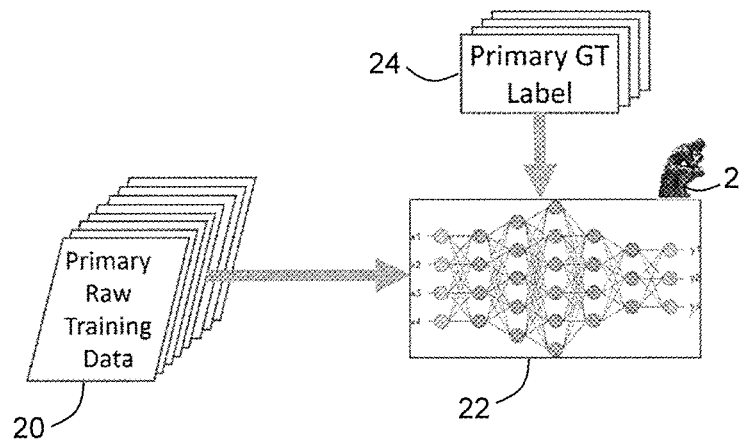
FIG. 2 is a flow chart illustrating in overview a method of training a classifier using a deep learning approach.
Figure 3:
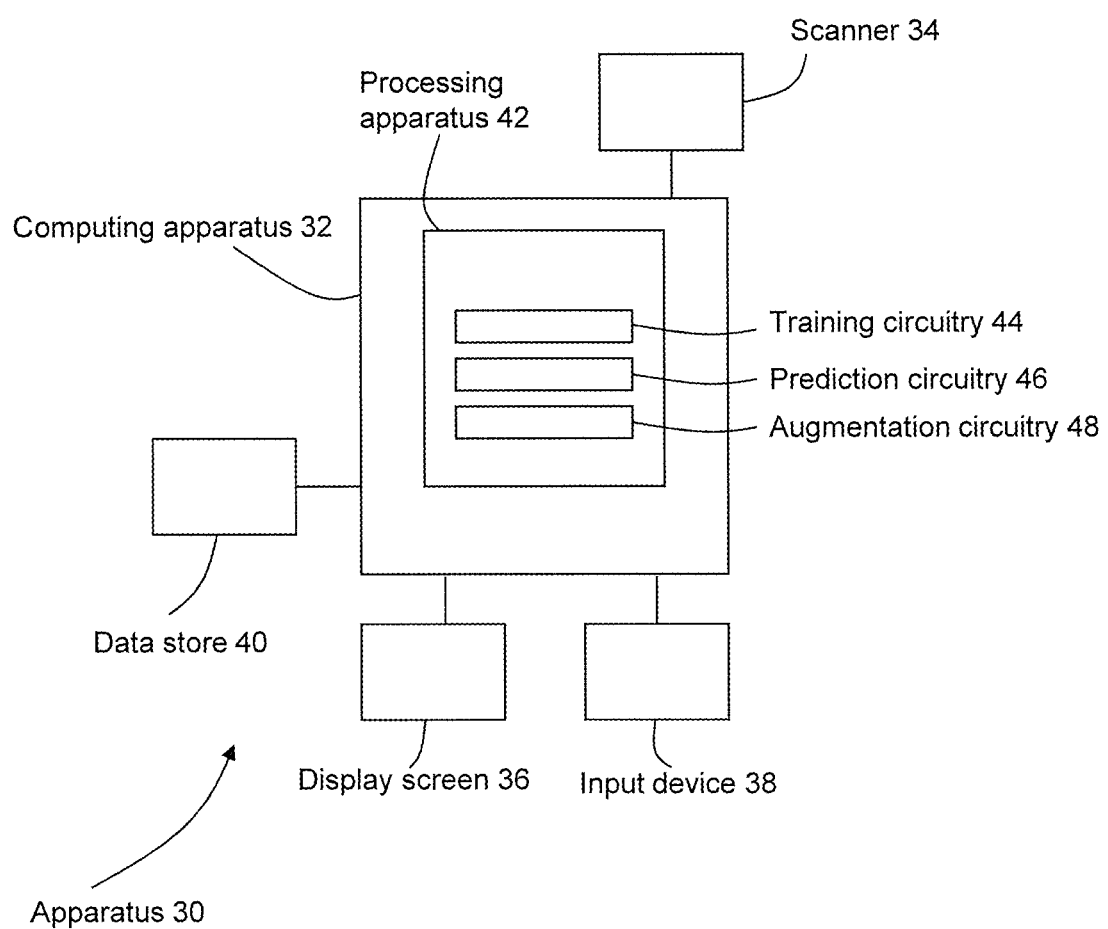
FIG. 3 is a schematic diagram of an apparatus according to an embodiment.

An image data processing apparatus 30 according to an embodiment is illustrated schematically in FIG. 3. In the embodiment of FIG. 3, the apparatus 30 is configured to train a neural network to predict an output, and to use the trained neural network to predict the output on unseen data. In other embodiments, a first apparatus may be used to train the neural network and a second, different apparatus may use the trained neural network to predict the output. In further embodiments, any apparatus or combinations of apparatuses may be used.

In further embodiments, the apparatus 30 may be configured to train any appropriate type of model, for example any appropriate machine learning or artificial intelligence model. In some embodiments, the model does not comprise a neural network.

The image data processing apparatus 30 comprises a computing apparatus 32, in this case a personal computer (PC) or workstation, which is connected to a scanner 34, one or more display screens 36 and an input device or devices 38, such as a computer keyboard, mouse or trackball.

The scanner 34 may be any scanner that is configured to perform medical imaging. The scanner 34 is configured to generate image data that is representative of at least one anatomical region of a patient or other subject. The scanner may be configured to obtain two-dimensional or three-dimensional image data in any imaging modality. For example, the scanner 34 may comprise a magnetic resonance (MR) scanner, CT (computed tomography) scanner, cone-beam CT scanner, X-ray scanner, ultrasound scanner, PET (positron emission tomography) scanner or SPECT (single photon emission computed tomography) scanner. In further embodiments, the scanner may generate any type of image data, which may not be medical image data.

In the present embodiment, image data sets obtained by the scanner 34 are stored in data store 40 and subsequently provided to computing apparatus 32. In an alternative embodiment, image data sets are supplied from a remote data store (not shown) which may form part of a Picture Archiving and Communication System (PACS). The data store 40 or remote data store may comprise any suitable form of memory storage.

In further embodiments, any suitable type of data may be used to train the model. The data may have been obtained from any suitable data gathering device, which may or may not comprise a scanner. The data may have been retrieved from any suitable data storage. In some embodiments, the training data does comprise image data and/or the data to which the trained model is applied does not comprise image data.

Computing apparatus 32 comprises a processing apparatus 42 for processing of data, which in this embodiment includes image data. The processing apparatus comprises a central processing unit (CPU) and Graphical Processing Unit (GPU).

In the present embodiment, the processing apparatus 42 provides a processing resource for automatically or semi-automatically processing image data sets. For simplicity, we will refer below to the processing of medical images. However, in practice, the operations described below may be performed on any suitable sets of image data that are representative of medical images. Image data may be processed internally by the processing apparatus 42 without any corresponding image being displayed.

The processing apparatus 42 includes training circuitry 44 configured to train a model to predict an output and prediction circuitry 46 configured to use the trained model to predict the output. In some embodiments, the processing apparatus 42 further comprises augmentation circuitry 48.

In the present embodiment, the circuitries 44, 46, 48 are each implemented in the CPU and/or GPU by means of a computer program having computer-readable instructions that are executable to perform the method of the embodiment. In other embodiments, the various circuitries may be implemented as one or more ASICs (application specific integrated circuits) or FPGAs (field programmable gate arrays).

The computing apparatus 32 also includes a hard drive and other components of a PC including RAM, ROM, a data bus, an operating system including various device drivers, and hardware devices including a graphics card. Such components are not shown in FIG. 3 for clarity.

Embodiments are described below with reference to FIGS. 5 to 11.

Figure 4:
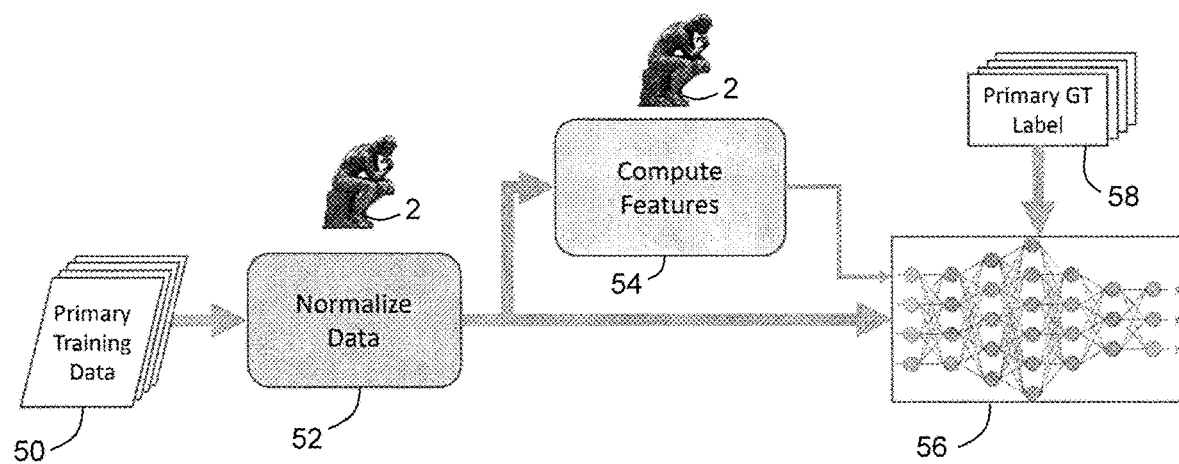
FIG. 4 is a flow chart illustrating in overview a method of training a neural network.

FIG. 4 is a flow chart illustrating in overview an example of a method of training a neural network 56 using a combination of traditional pattern recognition with deep learning. The method of FIG. 4 is then compared to the embodiments of FIGS. 5 to 11, in which expert input is used in training a neural network.

In the method of FIG. 4, a training system normalizes then computes features. The features are provided as additional inputs to a neural network, which may also be referred to as a deep learning network.

A training system receives a plurality of sets of primary training data 50 and primary GT labels 58 for the primary training data. The primary GT labels have been obtained prior to the training. For example, the sets of primary training data 50 may have been manually classified to obtain the primary GT labels. The primary GT labels may provide information about any suitable characteristic of the training data, for example the presence or absence of a pathology.

At stage 52, a domain expert 2 performs a normalization of the primary training data 50. The normalized primary training data that is output from stage 52 is provided to the neural network 56.

The normalized primary training data that is output from stage 52 is also used as input to stage 54. At stage 54, the domain expert 2 selects a plurality of features. Values for the selected features are computed by the training system for each set of normalized training data. The computed values for the features are provided to the neural network 56.

The primary training labels 58 are also provided to the neural network 56. The neural network 56 undergoes a training process in which it learns to predict labels based on the normalized training data and the computed values for the features.

The training process results in a trained classifier which comprises the trained neural network. The trained classifier is trained to receive a target data set as input, and to output a predicted label for the target data set. For example, the output may comprise a classification of the target data set as including a pathology, or as not including that pathology.

In the exemplary method shown in FIG. 4, the data normalization and feature computation steps are also included in the delivered classifier. In order to use the trained neural network to predict a label for a target data set, the target data set is normalized and the normalized target data set is provided to the trained neural network. Features are computed from the normalized target data set and provided to the trained neural network. The trained neural network predicts a label for the target data set based on the normalized target data set and computed features.

In the method of FIG. 4, the computed features are determined solely by the domain expert 2. The computed features may be considered to be hardwired. The computed features are unable to evolve with the deep learning. For example, the neural network is unable to select further features that may be more predictive of the labels.

In contrast, in embodiments described below with reference to FIGS. 5 to 11, a neural network is trained such that the trained neural network is configured to receive a target data set as input, and to output a prediction (for example, a predicted label). No additional normalization or feature computation step is used once the neural network is trained. A predictor (for example, a classifier) may be obtained which comprises only a neural network. The predictor may be described as a pure neural network.

Embodiments of training methods described below may deliver a pure neural network which may be efficiently run on a GPU.

Figure 5:
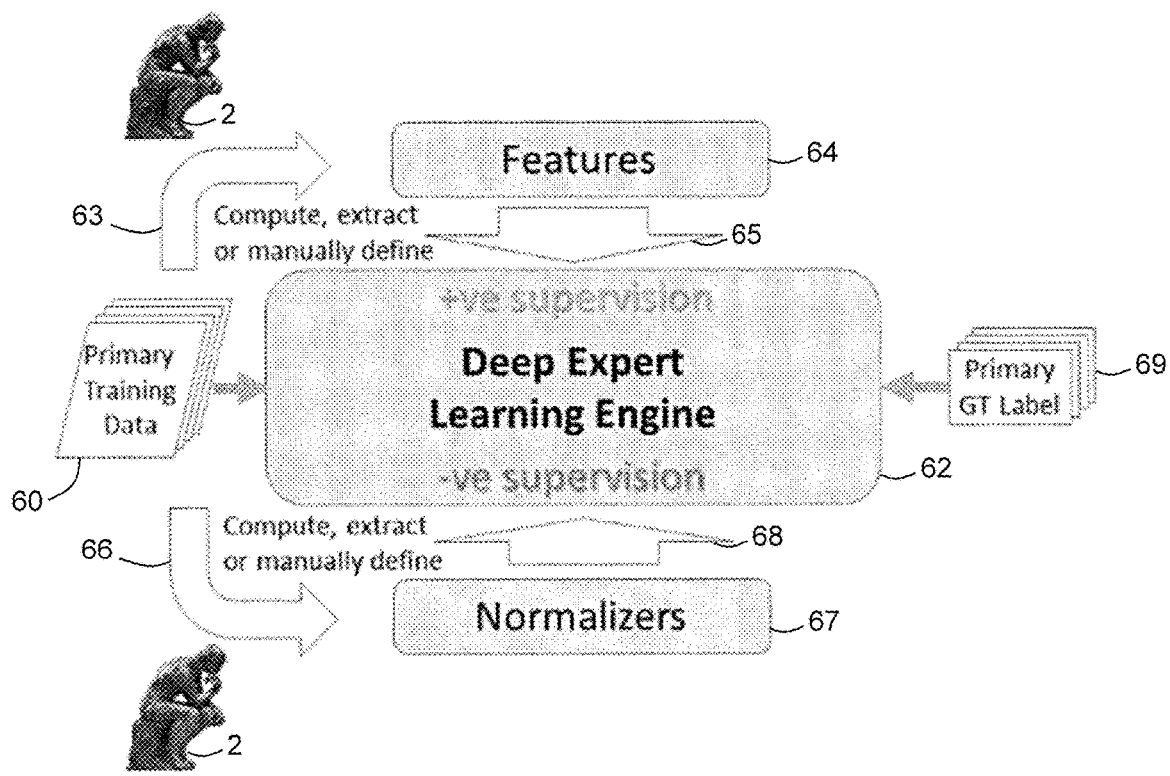
FIG. 5 is a flow chart illustrating in overview a method of training a neural network in accordance with an embodiment.

The training circuitry 44 is configured to perform a training method illustrated in overview in the flow chart of FIG. 5. In the method of FIG. 5, a domain expert's input is used to provide supervision to a neural network 62, which may also be described as a deep expert learning engine.

The training circuitry 44 receives a plurality of sets of training data 60. In the present embodiment, each set of training data 60 comprises a respective set of medical imaging data, for example a set of pixel or voxel intensities for an array of pixel or voxel positions. Each of the sets of training data 60 has been manually classified to obtain a ground truth label for each of the sets of training data.

At least some of the sets of training data also comprise values for further characteristics in addition to the image data and ground truth labels. The values for the further characteristics provide additional information that is used in the training of the neural network. Different ones of the sets of training data may comprise values for different ones of the further characteristics.

In the present embodiment, at least some of the sets of training data 60 comprise data concerning the image acquisition, for example DICOM data. For example, the data concerning the image acquisition may comprise details of the scanner, modality and/or protocol used to acquire the image; an institution or geographical location where the image was acquired; and/or a date on which the image was acquired. At least some of the sets of training data 60 may also comprise data that has been obtained by manually or automatically processing the image data. For example, some of the sets of training data may comprise organ segmentations or volumes, measured shapes or textures, physiological measurements, or clinical scores. At least some of the sets of training data may comprise non-imaging clinical data, for example laboratory results. At least some of the sets of training data may comprise information about the patient, for example patient age, gender, height or weight.

Additional information that forms part of at least some of the sets of training data may broadly be considered to fall into one of three categories. A first category of additional information comprises information that is often readily available as part of the data set (for example, modality, institution, scale, gender). In some circumstances, information that falls into the first category may be provided for all of the sets of training data 60.

A second category of additional information comprises data that may be provided manually as auxiliary ground truth (for example, estimated volumes). In some circumstances, data in the second category may only be available for some of the sets of training data 60. Different data may be available for different sets of training data 60. For example, different measurements may be been performed on different sets of training data 60.

A third category of additional information comprises data that is computed by a pre-existing algorithm. For example, an organ segmentation may be obtained by applying a known algorithm to training data sets. In some circumstances, a pre-existing algorithm (for example, an organ segmentation algorithm) may have been applied to some sets of training data, but may not have been applied to other sets of training data. In some circumstances, it may only be possible to apply the pre-existing algorithm to some of the sets of training data. For example, the pre-existing algorithm may require additional inputs that are only available in some of the sets of training data, or the pre-existing algorithm may only be applicable to certain modalities or types of acquisition.

The training data 60 may be considered to be heterogeneous. The training data 60 may be heterogeneous in that different types of information are available for different sets of training data. For example, some of the sets of training data may comprise only image data, while others of the sets of training data also comprise values for other characteristics, for example segmentations, measurements and/or other additional information. The training data 60 may additionally or alternatively be heterogeneous in the sense that the training data 60 comprises images of different modalities and/or other differences in image acquisition.

The training circuitry 44 provides the sets of primary training data 60 to the neural network 62.

A primary input of the neural network is defined by the training circuitry 44. The primary input comprises the data item or data items that will eventually be used as input to the trained neural network. In the present embodiment, the primary input comprises the image data.

The primary input comprises a type of data that is available for every data set in the cohort of training data 70. The primary input forms part of every data set used for training and every data set on which the trained neural network is deployed. The primary input is the input that is used by the deployed solution to obtain a prediction.

In some embodiments, the primary input is defined by the domain expert 2. For example, the domain expert 2 may be provided with information about the training data 60 via a graphical user interface. Data types that are common to all of the training data may be highlighted in the graphical user interface.

A primary output of the neural network is defined by the training circuitry 44. In some embodiments, the primary output may be defined by the domain expert 2, for example via a graphical user interface as described above. In the present embodiment, the neural network is trained to perform a classification, and the primary output is a label. In other embodiments, the neural network may provide any suitable output. For example, the output may comprise a segmentation. The segmentation may be considered to provide a respective classification at every pixel or voxel.

In the present embodiment, ground truth data for the primary outputs need not be available for the whole cohort of training data. For example, ground truth labels may be available for only some of the sets of training data. In the present embodiment, the neural network is trained to predict the presence or absence of a pathology of interest.

At stage 63 of the process of FIG. 5, the domain expert 2 selects a plurality of features 64 in the training data 60 that the domain expert 2 considers to be related to the pathology of interest. The features 64 may also be referred to as positive characteristics. The features 64 are chosen from the set of characteristics for which values are available in at least some of the training data sets.

The selection of features 64 by the domain expert 2 is based on the domain expert's experience and knowledge. For example, the domain expert 2 may know that the position of the coronary artery, if available, is useful in determining whether the pathology is present.

Examples of features 64 selected by the domain expert 2 at stage 63 may include organ segmentations or volumes; measured shapes or textures that are known (for example from the literature) to be correlated with the pathology of interest; or physiological measurements, such as calculated perfusion parameters.

The selected features may be features for which data is available in some but not all of the sets of training data 60. For example, the position of the coronary artery may have been manually defined for a few of the sets of training data 60, which may be considered to form a first subset of the sets of training data 60. Values for another feature may be available only in a second, different subset of the sets of training data 60.

The selected features may comprise any suitable characteristics that are discernable from at least some of the sets of training data, for example characteristics for which values are included in at least some of the sets of training data or may be derived from at least some of the sets of training data.

The selected features may fall into one or more of the three categories described above: available as part of the training data; provided manually as auxiliary ground truth; or computed by a pre-existing algorithm.

These characteristics might be available for only part of the training cohort, and are not used in product deployment.

The training circuitry 44 and/or the domain expert 2 obtains values for each of the features 64 in at least some of the sets of training data. The values for the selected features 64 may be obtained in any suitable manner. For example, the values for the selected features 64 may be computed from the training data. The values for the selected features 64 may be extracted from the training data. The values for the selected features 64 may be manually defined by the domain expert 2 or by a further expert. For example, in a case where one of the selected features 64 is a segmentation, the domain expert 2 may manually segment one of the sets of training data, for example by annotating an image that has been generated using the set of training data.

At stage 65, the values for the selected features 64 are provided to the neural network 62 to be used in supervision. The supervision performed using the selected features 64 may be referred to as positive supervision. Positive supervision is discussed further below with reference to FIG. 6. In overview, positive supervision comprises indicating to the neural network that the selected features 64 are relevant to the classification for which the neural network is being trained.

At stage 66 of FIG. 5, the domain expert 2 selects a plurality of normalizers 67 in the training data 60 that the domain expert 2 considers to be unrelated to the pathology of interest. The normalizers may also be referred to as negative characteristics. The normalizers 67 are chosen from the set of characteristics for which values are available in at least some of the training data sets.

The selection of normalizers by the domain expert 2 is based on the domain expert's experience and knowledge. For example, the domain expert 2 may select as normalizers characteristics that are known to be a spurious consequence of data acquisition, and so are not related to the pathology of interest.

Examples of normalizers 67 selected by the domain expert 2 at stage 66 may include scanner manufacturer or acquiring instruction; image modality or enumerated protocol variant; image scale, intensity or acquisition direction (for example, in planar X-ray whether the acquisition is anterior-posterior or posterior-anterior); or the presence of imaging artefacts.

The selected normalizers 67 may be characteristics for which data is available in some but not all of the sets of training data 60. For example, values for a first normalizer may be available only in a third subset of the sets of training data 60. Values for a second normalizer 67 may be available only in a fourth subset of the sets of training data 60.

The selected normalizers 67 may comprise any suitable characteristics that are discernable from at least some of the sets of training data, for example characteristics for which values are included in at least some of the sets of training data or may be derived from at least some of the sets of training data. The selected normalizers 67 may fall into one or more of the three categories described above: available as part of the training data; provided manually as auxiliary ground truth; or computed by a pre-existing algorithm.

Values for the normalizers 67 might be available for only part of the training cohort. Values for the normalizers 67 are not used in product deployment.

The training circuitry 44 and/or the domain expert 2 obtains values for each of the normalizers 67 in at least some of the sets of training data. The values for the selected normalizers 67 may be obtained in any suitable manner. For example, the values for the selected normalizers 67 may be computed from the training data. The values for the selected normalizers 67 may be extracted from the training data. The values for the selected normalizers 67 may be manually defined by the domain expert 2 or by a further expert.

At stage 68, the training circuitry 44 provides the computed values for the normalizers 67 to the neural network 62 to be used in supervision. The supervision performed using the normalizers 67 may be referred to as positive supervision Negative supervision is discussed further below with reference to FIG. 6. In overview, the negative supervision comprises indicating to the neural network that the selected normalizers are irrelevant to the classification for which the neural network is being trained. In other embodiments, the normalizers may comprise parameters that are considered to be less relevant than other parameters, for example parameters that are considered to be of marginal relevance.

The training circuitry 44 also provides the neural network 62 with primary ground truth labels 69 for at least some of the sets of training data 60.

Using the primary GT labels 69 and primary training data 62, the training circuitry 44 is trained to perform a classification process to predict labels from primary input data. In this embodiment, the primary input data comprises image data. Positive supervision is used to train the neural network 62 to be sensitive to the selected features 64, for example to assign positive weights to the selected features. Negative supervision is used to train the neural network 62 to be insensitive to the selected normalizers 67.

In the method of FIG. 5, normalization and feature measurement are incorporated into a neural network approach through the addition of deep supervision. Normalization is viewed as negative supervision and is implemented through adversarial training.

Feature measurement is viewed as auxiliary positive supervision at intermediate levels of the neural network, which may be considered to be similar to deeply supervised networks, but using intermediate features which may be computed, provided as manual GT or extracted from imaging metadata.

Figure 6:
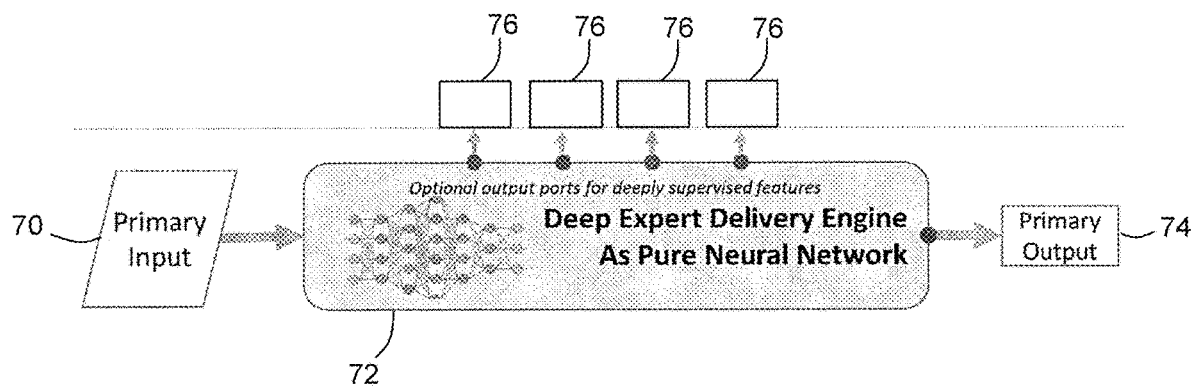
FIG. 6 is a flow chart illustrating in overview the deployment of a trained neural network in accordance with an embodiment.

FIG. 6 illustrates in overview a deployment of a trained neural network 72 that has been trained in accordance with the method of FIG. 5. In the embodiment of FIG. 6, the trained neural network 72 is stored in data store 40 or in an alternative data store. When used, it is installed from the memory and read out to the prediction circuitry 46. In other embodiments, the trained model may be preset on prediction circuitry using, for example, at least one ASIC or FPGA.

The prediction circuitry 46 provides a primary input 70 to the trained neural network 72. The type of data included in the primary input 70 was defined when training the neural network 72. In the present embodiment, the primary input 70 comprises a set of image data. In other embodiments, the primary input 70 may comprise any suitable type of data.

The prediction circuitry 46 does not pre-process the primary input data 70 to perform normalization or feature measurement.

The neural network 72 (which may also be referred to as a deep expert delivery engine) outputs a primary output 74. The primary output 74 may also be referred to as a predicted output. In the present embodiment, the neural network 72 outputs class labels that it was trained to predict using the method of FIG. 5. In other embodiment, the primary output may comprise any suitable predicted output or outputs, for example any suitable regression, detection, score or segmentation.

In addition to the primary output, the neural network 72 may also output one or more further outputs 76. The further outputs 76 may comprise outputs of those features that were provided during training. In some circumstances, providing values for features that the domain expert considered to be relevant may help to explain to a clinician how the neural network arrived at a particular result.

In the embodiment of FIGS. 5 and 6, the deep expert concept creates a streamlined pure neural network requiring only the primary data as input.

Normalization and feature extraction are viewed as negative and positive (respectively) deep supervision, acting as regularizers which add constraints which may mitigate the impact of small training datasets. It is the domain expert's task to decide which characteristics of the data represent spurious variation and should be treated as negative supervision (normalization), and which represent variation that is significant to the classification task at hand, and so should be treated as positive supervision (features). Ideas of deep supervision and adversarial training are adapted to show how these concepts can be implemented in a deep neural network framework. The methodology delivers a classifier as a pure neural network, with no pre-processing for normalization or feature extraction.

FIG. 5 provides a simple illustration of a learning phase, and FIG. 6 provides a simple illustration of deployment in a product. FIG. 5 may be considered to provide an external black-box view of the deep expert concept at training time.

Figure 7:
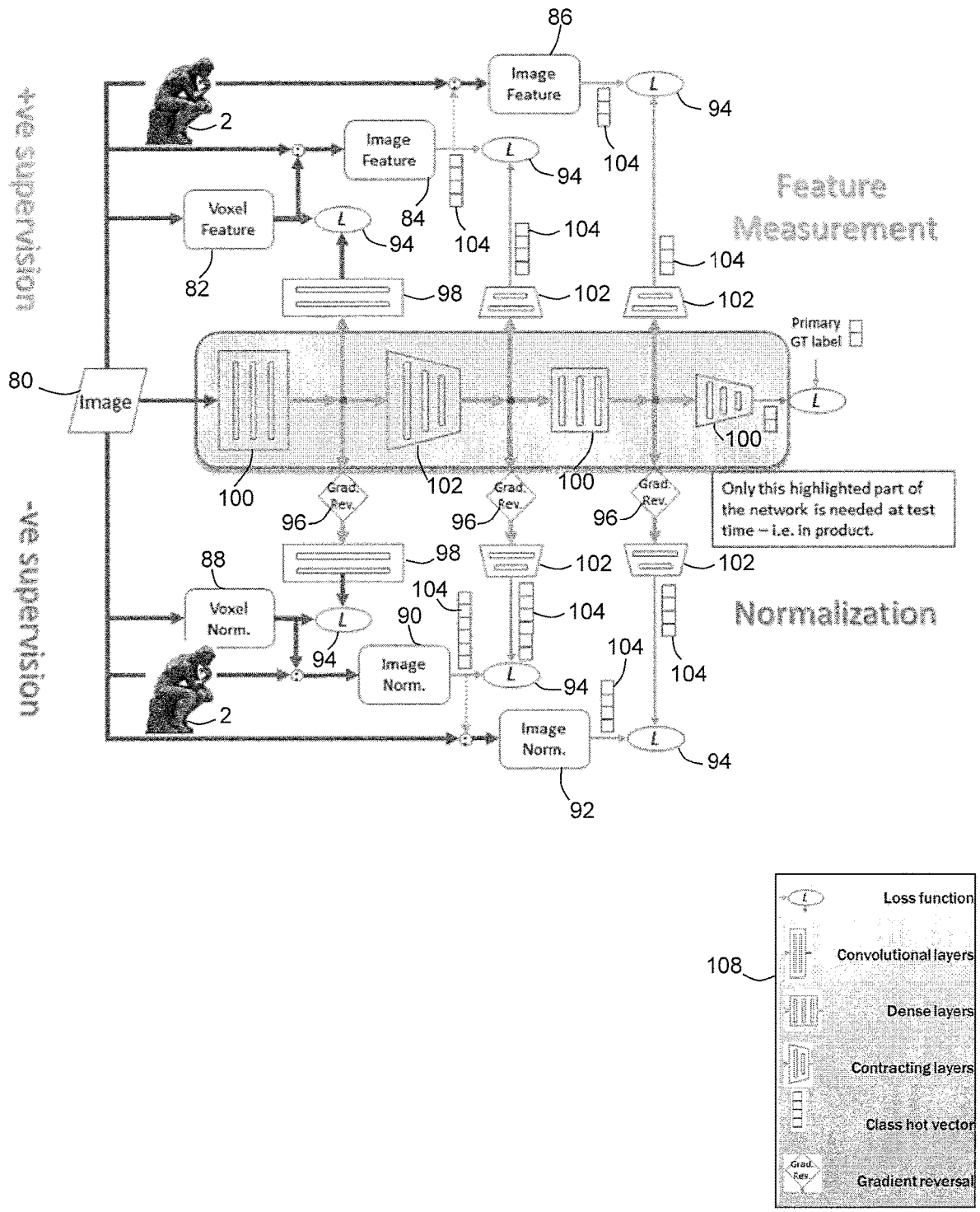
FIG. 7 is a flow chart illustrating in overview a method of training and deploying a neural network in accordance with an embodiment.

A generic neural network capable of implementing the learning and delivery engine of FIGS. 5 and 6 is shown in FIG. 7. FIG. 7 shows a network illustrating normalization and feature measurement through deep supervision. A key 108 indicates the symbols used in FIG. 7.

Image data 80 is provided to a neural network. At the top part of the network as shown in FIG. 7, the domain expert 2 selects a plurality of features to be used for positive supervision. In the embodiment shown in FIG. 7, the selected features are a voxel feature 82, image feature 84, and image feature 86. It may be considered that feature measurement is modelled in the top half of the network. Properties believed to be helpful, whether computed or manually provided, are used to encourage the emergence of representations in which these properties (features) are apparent.

At the bottom half of the network as shown in FIG. 7, the domain expert 2 selects a plurality of normalizers to be used for negative supervision. In the embodiment shown in FIG. 7, the selected normalizers are a voxel normalizer 88, image normalizer 90, and image normalizer 92.

The features 82, 84, 86 and normalizers 88, 90, 92 are provided to respective loss functions 94.

A difference between the top part of the network (features) and the bottom half (normalizers) is that a gradient reversal stage 96 is applied to the normalizers. The gradient reversal encourages representation in which the to-be-normalized characteristics identified by the normalizers 88, 90, 92 are not discernable.

Various convolutional layers 98, dense layers 100 and contracting layers 102 are shown in FIG. 7. In other embodiments, any suitable combination of layers can be used. FIG. 7 also represents a plurality of class hot vectors 104. The network of FIG. 7 is configured to output a predicted label 112.

The part of the network of FIG. 7 that is deployed after training is indicated in FIG. 7 as network 110. In use, an image 80 is provided to network 110, which outputs a predicted label 112 without explicitly calculating the features 82, 84, 86 or normalizers 88, 90, 92. Only the network 110 is needed at test time, i.e. in a final product. The use of only trained network 110 at test time may result in a streamlined, efficient delivered solution.

The method of FIGS. 5, 6 and 7 may be considered to incorporate benefits of normalization and feature measurement without the eventual trained classifier having to include normalization and feature measurement steps. In the method of FIGS. 5, 6 and 7, normalization and feature measurement are incorporated through the addition of deep negative and positive supervision. Normalization may be seen as negative supervision. Feature measurement may be seen as positive supervision.

Deep supervision characteristics, whether negative (normalization) or positive (feature measurement) are required only at training time. The deep supervision characteristics can be arithmetically computed from the data as would be the case in classic feature measurement, or can be provided as manual ground truth. Some characteristics such as modality, institution and image scale may be trivially extracted from imaging metadata. In many cases, the domain expert's task may be simply to decide which characteristics represent positive supervision and which represent negative supervision.

The available training data may be highly variable in regard to the information available. For example, different sets of training data may include different data types. Different sets of training data may be acquired using different modalities. Cohorts for training algorithms for analyzing medical data, for example algorithms for image analysis and clinical decision support systems may be small, which may lead to poor generalization in the absence of involvement from clinical domain experts. In some circumstances, available data may need to be assembled from heterogeneous unconsented subsets (e.g. from a Safe Haven), which may be considered to form a patchwork of available data and ground truth. The available data and ground truth may in some cases be unsuitable for direct deep learning. In the embodiments of FIGS. 5 to 7, solutions are created by combining deep learning methods with expert (typically clinical) domain knowledge. The domain expert's knowledge may be used as efficiently as possible, in a method which may allow the domain expert to express their wisdom with minimal support from programmers and machine learning experts.

In conventional approaches (whether traditional pattern recognition or deep learning) where information in the training data is viewed as data inputs that are required at training time and test time, then the issue of missing data may cause difficulties. In the above embodiments, any issues of heterogeneity may only concern training time. In the context of deep neural networks trained by stochastic gradient descent, a reasonable approach may be to construct specialized training batches from sub-sets of training samples for which label Y is available to train the network branch with terminates in Loss(Y).

The training of each network branch may be balanced. At each branch point in the network, a factor may be used to weight the contribution of back propagated gradients.

In the embodiments of FIGS. 5 to 7, rather than pursuing generic regularization techniques, expert domain knowledge is systematically incorporated. It may be considered that a central problem of machine learning is to choose one predictive function $f()$ from a large (often very large) space of hypothesized functions H, given only a limited number of training samples. Deep learning may offer very large hypothesis spaces, and so there may be a large subset of the space of hypothesized functions H that correctly predict the training data. The subset of the space of hypothesized functions H that performs well on the wider population may be much smaller.

Figure 8:
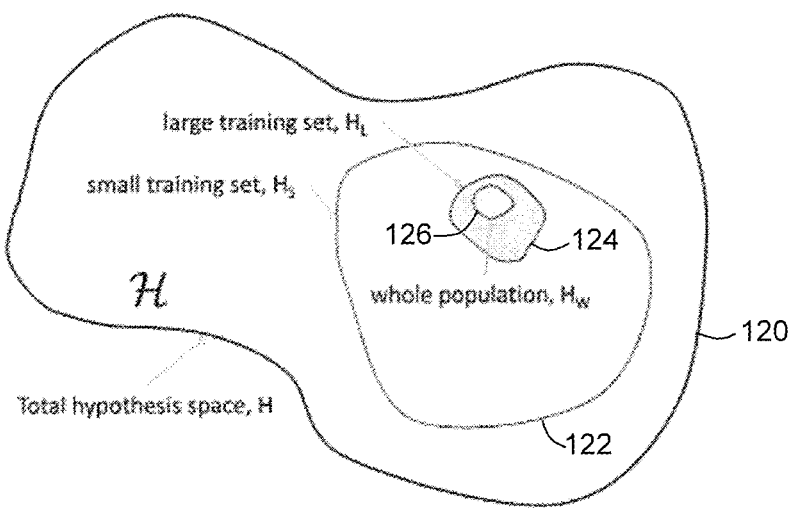
FIG. 8 is a schematic illustration of a hypothesis space H.

FIG. 8 is a schematic illustration of hypothesis space H, 120 comprising a large plurality of hypotheses. A subset of hypotheses giving an acceptable miscalculation risk for a small training set is indicated as $H_S$, 122. A subset of hypotheses giving an acceptable miscalculation risk for a large training set is indicated as $H_L$, 124. The subset that would be acceptable in the whole population is indicated as $H_W$, 126.

With a small training set, $H_3$ is much larger than the desired $H_W$, and thus it may be likely that a trained solution will be outside $H_W$ and so will perform poorly. With small training sets, hypothesis selection may be under-constrained.

In embodiments described above with reference to FIGS. 5, 6 and 7, expert domain knowledge is used to rule in likely successful regions of H and to rule out regions that are likely to be unsuccessful.

With reference to the terminology of traditional pattern recognition methodology, ruling in regions that are likely to be successful may be considered to relate to feature measurement. Ruling out regions that are likely to be unsuccessful may be considered to relate to normalization.

Figure 9:
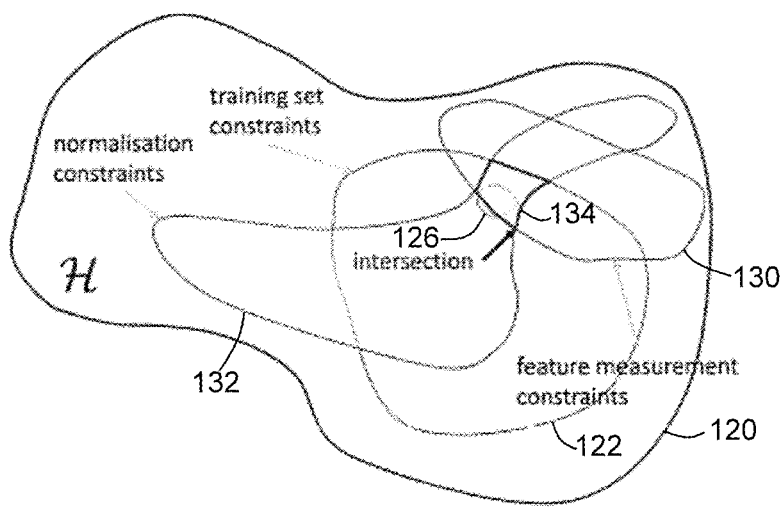
FIG. 9 is a further schematic illustration of the hypothesis space H.

FIG. 9 is a further illustration of the hypothesis space H, 120 that is shown in FIG. 8. FIG. 9 shows the subset $H_3$, 122 of hypotheses that is provided by the small training set and the subset $H_W$, 126 that would be acceptable in the whole population. FIG. 9 also represents the constraints on the hypothesis space that are provided by normalization and feature measurement. A subset 130 of the hypothesis space gives an acceptable miscalculation risk based on the feature measurement constraints provided by the expert. A subset 132 of the hypothesis space gives an acceptable miscalculation risk based on the normalization constraints provided by the expert. It may be seen that an intersection 134 of the subsets 122, 130, 132 is a closer fit to the subset $H_W$ than would be provided by the training data alone. The combination of expert knowledge expressed as normalization and feature measurement, combined with empirical information from the training set, results in an intersection 134 that is more tightly constrained around $H_W$.

In the embodiments described above, heterogeneous sets of training data are used to train the neural network. The sets of training data may comprise image data acquired using different modalities. Different sets of training data may also comprise additional data having different data types. The number of sets of training data available may be relatively small.

In further embodiments, data augmentation and/or data synthesis is used to artificially generate additional, synthetic sets of training data on which the neural network is trained.

Data augmentation may comprise a process whereby training data is replicated and modified in plausible ways, given an understanding of the data acquisition process. Alternatively or additionally, data can be synthetically generated from a parameterized model. For example, we might perturb image translation, rotation, isotropic scale, brightness/contrast. A single set of training data may be modified in multiple ways to obtain multiple further sets of training data.

It is known that data augmentation (or synthesis) may improve generalization when training data is in short supply.

Data augmentation is a process whereby available training data is replicated and modified in plausible ways, given an understanding of the data acquisition process, without affecting characteristics considered relevant to classification task. It is a well-known and much used means of compensating for paucity of training data. Data augmentation uses domain knowledge to understand the modes of variation present.

Use of synthetic training data is also widely known. Data synthesis may comprise constructing artificial data sets instead of using or modifying real data sets from real image acquisitions. Data synthesis may require some hand-crafted model able to generate plausible examples (for example, images) that are representative of the classes of interest.

Adversarial domain adaptation may be applied when a mixture of real and synthetic data are used to train a network, encouraging the network to find features which are blind to the real vs synthetic status of the data.

Real and synthetic may be treated as different domains. A branch of the network may attempt adversarially to tell the difference between real and synthetic, thus resulting in intermediate representations which are substantially invariant to differences between real and synthetic cases.

Data augmentation and synthesis may be considered together. Both data augmentation and synthesis may be considered to imply a computational model with parameterization which we perturb to generate plausible examples. Augmentation in particular may be seen as a form of regularization fulfilling a similar role to normalization in traditional pattern recognition. The parameter space could be quite large, having many dimensions. In volume imaging cases we may wish to perturb parameters including, for example, translation (3 dimensions), rotation (3 dimensions) isotropic scale (1 dimension), brightness/contrast (2 dimensions), bias field (several dimensions). In some cases, an image may be flipped, for example by reversing a horizontal or vertical axis. There may easily be around 10 parameters to be sampled from. To cover this space with even only three examples per axis would require $3^{10} \approx 59,000$ augmentations. Such numbers would overwhelm training.

In a conventional approach to augmentation or synthetic data generation, we are generating examples and leaving the ML algorithm (for example the neural network) to figure out what is and is not important: what variation is spurious and what significant.

In the embodiment described below with reference to FIG. 10, it is considered that we already know the parameterization of the augmented (or synthesized) parameters, so we can tell the network directly. In the case of augmentation, the sampling parameters of the augmentation are passed to the neural network as deep negative supervision variables, thus explicitly encouraging the network to find representations which are invariant to these perturbing factors.

In the case of synthetic data generation, some of the parameters may represent spurious variation (to be treated as deep negative supervision as with augmentation) while others may directly relate to the discrimination task in hand, and so should be provided as deep positive supervision. When provided with this additional information, which is readily available, the network should be able to learn what the augmented or synthetic data is trying to teach it, more reliably and with far fewer examples.

Figure 10:
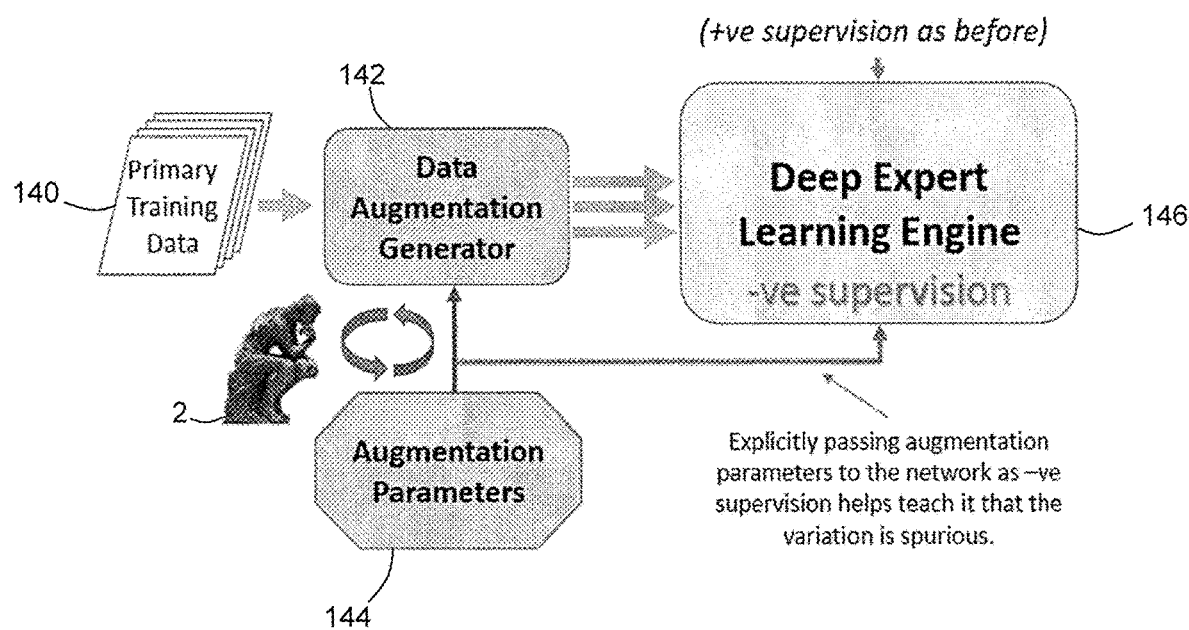
FIG. 10 is a flow chart illustrating in overview a method of training a neural network in accordance with an embodiment.

FIG. 10 is a flow chart illustrating in overview a method of training a neural network in accordance with an embodiment. The augmentation circuitry 48 receives a plurality of sets of training data 140. Similarly to embodiments described above, the training data is heterogeneous. The number of sets of training data may be considered to be relatively small. Some types of data (for example, segmentations or labels) may only be available for some, but not all, of the training data.

The augmentation circuitry 48 also receives a set of augmentation parameters 142. The augmentation parameters 142 are parameters that are to be perturbed to obtain further sets of training data.

The augmentation parameters 142 are selected to be parameters that are not important to the desired output of the neural network. For example, one would expect that the classification of an image in a training data set should be the same regardless of a degree of rotation of that image.

In an embodiment, the augmentation parameters 142 comprise image translation, rotation, isotropic scale, brightness and contrast.

At stage 144, the augmentation circuitry 48 perturbs each of the sets of training data to obtain further, synthetic sets of training data. For each set of training data, the augmentation circuitry 48 creates at least one further, synthetic set of training data by modifying a value for at least one of the augmentation parameters. In some embodiments, for each set of training data, the augmentation circuitry 48 generates multiple further, synthetic sets of training data by modifying values for multiple ones of the augmentation parameters 142 and/or by modifying a value for one of the augmentation parameters 142 by different amounts. In some embodiments, the creation of synthetic sets of training data may be used to increase the number of sets of training data to between twice the original number of sets of training data and ten times the original number of sets of training data. The modification of the parameters may be performed in a random, semi-random or pseudorandom fashion. Random sampling of the parameter space within limits defined for each parameter may provide better results than a regular sampling of the parameter space, for example a grid-based sampling.

The augmentation circuitry 48 passes the sets of training data and the further, synthetic sets of training data to the training circuitry 44, which is configured to train a neural network 146. The neural network 146 may also be referred to as a deep expert learning engine.

The augmentation circuitry 48 also passes the augmentation parameters 142 to the neural network 146 as negative supervision. Explicitly passing augmentation parameters 142 to the neural network 146 as negative supervision may help to teach the neural network 146 that the variation due to the augmentation parameters 142 is spurious. Augmentation may be used to teach the neural network 146 how to better normalize away spurious variation. The neural network 146 is explicitly told that the variation in the values for the augmentation parameters 142 is irrelevant, encouraging the neural network 146 to find features which are invariant to the values of the augmentation parameters 142.

Positive supervision of the neural network 146 may be performed as described above with reference to the methods of FIG. 5 and FIG. 7.

More effective data augmentation may be achieved by informing the learning engine of perturbed parameters.

Figure 11:
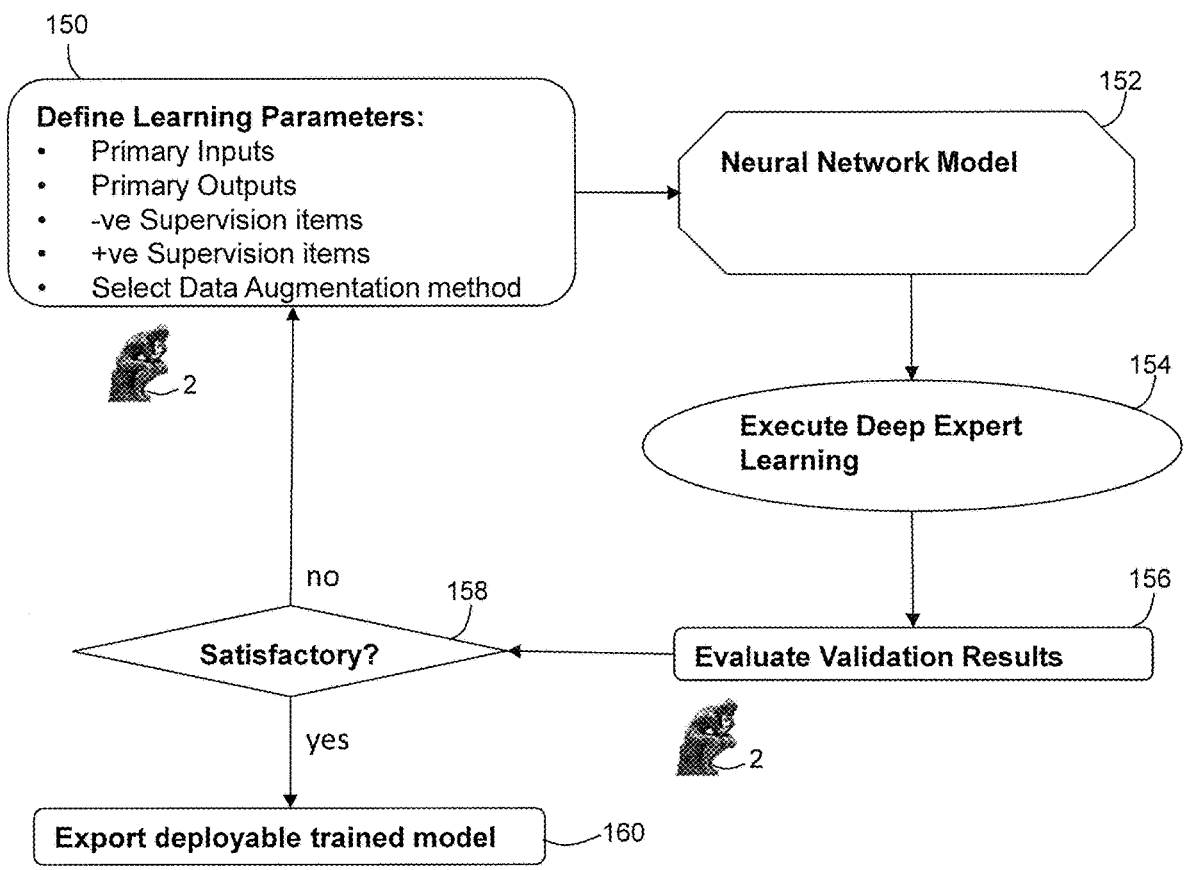
FIG. 11 is a flow chart illustrating in overview a method of an embodiment.

FIG. 11 is a flow chart illustrating in overview a method of an embodiment. The embodiment provides an interactive system for expressing domain knowledge. A domain expert 2 with access to a cohort of mixed data is allowed to express their domain knowledge and to create algorithms which will deploy efficiently on a GPU equipped machine.

At stage 150, the domain expert 2 defines a set of learning parameters. The learning parameters comprise primary inputs, primary outputs, negative supervision items, positive supervision items, and a data augmentation method.

It is through the selection of positive and negative supervision characteristics that the domain expert 2 imparts his/her knowledge and understanding. The selection of learning parameters by the domain expert 2 may be more efficient than explicitly coding normalization and feature extraction algorithms.

A computer system used by the expert 2 is configured to browse a cohort of available data sets. For example, the expert 2 may be able to see which types of data are available for each data set which is available for use in training.

The computer system is further configured to view a summary of data items available within the cohort of available data sets. For each data item, the summary gives counts. For example, the summary may count how many cohorts include segmentation data or labelling data. The summary may also provide simple distributions for each data item. The summary may provide statistics, for example mean, standard deviation, median and/or quartiles. The summary may provide connotational distributions. The connotational distributions may comprise distributions that are conditional on the value of a deflected categorical data item, for example a disease state. The summary may include clinical information and selected meta-information e.g. from DICOM headers.

We consider each of the learning parameters in turn.

The expert 2 selects the data item or data items which are to be the primary input or primary inputs for the algorithm. The primary input or inputs are chosen to be data items that are available for every data set in the cohort of data sets that is to be used for training. The computer system may assist the expert 2 by highlighting data items for which data is available for every data set in the cohort.

The expert 2 selects the data item or data items which are to be the primary output of the created solution, which may also be described as the primary ground truth. In the present embodiment, primary outputs need not be available for the whole cohort.

The expert 2 selects negative supervision items by selecting data items (for example, fields or properties), which the expert judges to represent spurious variation. Spurious variation may be variation that confounding to the classification task in hand. In the present embodiment, the negative supervision items include parameters of image acquisition and the contributing institute. The negative supervision items will be used by the system as negative supervision, encouraging data normalization. Negative supervision data items do not need to be available for the whole cohort.

The expert 2 selects positive supervision items by selecting data items judged to be informative of the primary classification goal. The positive supervision items include data items for which, if values for the data items were know, the values for the data items would assist with the classification task. The positive supervision items may include codified results obtained in a manner known from the literature. For example, the positive supervision items may include risk scores. Positive supervision data items do not need to be available for the whole cohort.

The expert 2 selects a data augmentation method. For example, the expert 2 may select the data augmentation method from a menu of options. The expert 2 may select augmentation parameters to be used with data augmentation. The expert 2 may select a method of synthesis to be used.

The learning parameters are provided to a neural network model 152. A plurality of training data sets is also provided to the neural network model 152. The training data sets are taken from the cohort of data sets for which information has been provided to the expert 2.

At stage 154, the neural network model executes deep expert learning. The deep expert learning may take many hours. The output of the deep expert learning stage 154 is a trained neural network.

At stage 156, the trained neural network is validated. For example, the trained neural network may be tested on further data sets from the cohort, which have not been used in the training of the neural network. Performance results based on cross-validation are output upon completion.

The expert 2 evaluates the validation results. At decision point 158, the expert determines whether the results output by the trained neural network are satisfactory. If the answer is no, the flow chart of FIG. 11 returns to stage 150. The expert 2 may select different learning parameters with which to train the neural network. For example, the expert 2 may select different positive supervision items and/or different negative supervision items.

If the answer at stage 158 is yes, the flow chart of FIG. 11 proceeds to stage 160. At stage 160, a deployable model is exported. A representation of the trained neural network model is output. The representation of the trained neural network model is made available to be installed on the current system or on other compatible systems. The representation of the trained neural network may be used for the rapid prediction of the defined primary outputs from the defined primary inputs.

We now consider an example of a use case for an example of a training method and trained neural network as described above. In this example, the training method and trained neural network are used for suspected stroke. The training method and trained neural network may be used for the detection of ischemia and/or the determination of ASPECT score (Alberta Stroke Program Early CT Score). The time critical nature of acute stroke is considered to require an efficient (quick runtime) product.

It is desired to provide a method that is effective in both NCCT (non-contrast computed tomography) and CTA (computed tomography angiography). The method is to be used in both thick-slice and thin-slice imaging. It is desired that the method is capable of working across a range of different manufacturers and reconstruction methods (for example, AIDR3D, FIRST).

The provision of such a method may be considered to be a weakly supervised problem.

We have available a small number (around 100) of datasets for which clinical ASPECT score is available. Further datasets (around 200) are available but without ASPECTS. The further datasets comprise a mix of normal datasets and abnormal datasets.

Various clinical data (for example, time since onset and affected laterality) is available for some of the datasets. However, availability of the clinical data is mixed. For example, time since onset may be available for one subset of the datasets. Affected laterality may be available for a further, different subset of the datasets.

Manual ischemia segmentation GT may be available for most but not all of this data. For some datasets we have additionally segmentation GT for thrombus. Dense vessel sign are often associated with ischemia. A clinically assessed ASPECTS score (a score from 1 to 10) is available for some datasets. The laterality (left or right) of clinical signs is available for some datasets.

Through the limited services of a neuroradiologist, ground truth of affected vascular territories has been recorded for some of the datasets. The neuroradiologist may also be able to record other information on a subset of datasets if asked.

Datasets may have come from disparate sources and/or may have different markers, resulting in a heterogeneity of available information.

Some stroke patients cannot keep their head in standard pose, and so datasets are sometimes rotated about the S-I (superior-inferior) axis by up to 25 degrees.

An expert provides knowledge or information to be used in training the neural network. Some invariances are known. It is known that the imaging modality used (whether NCCT or CTA) is not relevant to pathology. Slice thickness is also not relevant to pathology. Scanner manufacturer, reconstruction method, image acquisition scale, and the institution at which the datasets were acquired are not relevant to pathology. Although stroke imaging presents differently depending on time since onset, it is clear that the time since onset is unrelated to a severity of the stroke.

In stating the above invariances, we are considering the total population of datasets (not just the small sample of 100+200 training datasets in the development set). It may be the case that the training datasets have some bias, for example due to randomness of small samples. In some cases, bias may result from a more systematic reason, for example one institution imaging more normals than others. However, it is known that such bias is spurious.

It is known that ASPECTS is closely related to the presence or absence of ischemia in each of 10 standard vascular territories in each of the left and right side of the brain.

It is known that contra-lateral comparison is important. In particular, ischemic regions typically have slightly lower mean intensity (for example, intensity in Hounsfield units) than the contra-lateral region. For example, if ischemia is present in the left side of the brain, an image of the left side of the brain may have slightly lower mean intensity than a corresponding image of the right side of the brain.

It is known that an understanding of the vascular territories is important to ASPECTS determination.

We implicitly need to know the brain mid-line (plane) to perform contra-lateral comparisons (comparisons of the left side of the brain to the right side of the brain).

Laterality of symptoms is known to be related to laterality of ischemic regions.

It is also known that ischemia is typically caused by a thrombus (blood clot) which may be visible in imaging as a dense vessel sign.

It is considered that 100 datasets is inadequate for a traditional deep learning approach to a weekly supervised problem, particularly one as difficult as ASPECT scoring. In this example, the cohort of datasets may be considered to be poorly controlled, having different sub-modalities, scanner manufacturers, acquisition parameters etc., which may be a further indication that 100 datasets is inadequate for training.

One could consider a method along the lines of traditional pattern recognition and image analysis. Steps could be taken to normalize acquisition issues, for example by rescaling and re-slicing. One could consider developing separate algorithms for NCCT and for CTA, but that would divide the already limited training data. It may be the case that an algorithm is available that can detect brain mid-line, and a further algorithm is available that can segment vascular territories. One could then explicitly calculate contra-lateral HU differences and correlate with vascular territories and the small amount of ischemic region GT, and thereby obtain ASPECTS. However, such a method may be very complicated and may lack robustness.

The large heterogeneity of available information and GT may be considered to be further complicating factor, requiring the use of classifiers which can handle missing information.

It is noted that such heterogeneity is likely to be an increasingly common fact of life as we seek to train algorithms on un-consented patient data, within a safe haven, rather than from carefully curated research cohorts.

A traditional approach to classification may comprise a complex combination of algorithms which would need to be built into the delivered solution, having a negative impact on runtime.

The methodology described above with reference to FIGS. 5 to 7 does not wholly remove complexity for from the development phase, but it may be considered to remove complexity from the delivered classifier, and it does address the heterogeneity of available information.

Turning to the training of the neural network using the training datasets, the primary input is an NCCT volume, and the primary output is an ischemic region segmentation. Positive supervision items include dense vessels, ASPECTS score, and laterality. The positive supervision items are known to be relevant to the ischemic region segmentation. Negative supervision items include institution, scanner model, and slice thickness. The negative supervision items are known to be irrelevant to the ischemic region segmentation.

Data may be augmented using negative supervision as described above with reference to FIG. 10. For example, datasets may be augmented by changing a dataset rotation angle. Dataset rotation angle may be provided to the neural network as a negative supervision item.

The final trained network will require only the NCCT volume as input.

Expert prior knowledge or additional supervision information is exploited to improve the effectiveness of deep learning solutions in the presence of limited training data, implemented in such a way that the resulting solution remains a pure neural network, with the architectural simplicity and efficient GPU deployment that implies.

Certain embodiments provide a medical imaging system to allow a domain expert or user to train an algorithm, from heterogeneous datasets, i.e. where each available dataset has different imaging modalities and/or associated characteristics—'information items'. A method comprises:
a) Selecting datasets forming the training set.
b) Identifying information items required by the algorithm for input at deployment
c) Identifying additional optional training information items which encourage the discovery of relevant characteristics of the data
d) Identifying additional optional information items which encourage normalization of spurious characteristics of the data
e) Training a neural network in which items in b) and c) are handled by conventional positive supervision, while items in d) are handled by negative supervision using gradient reversal.
f) Creating an efficient deployable implementation of the algorithm which is a pure neural network without preprocessing, requiring as input only those information items in b) (items from c) and d) are not required at deployment.

Additionally, data augmentation may be applied using negative supervision of training augmentation parameters.

Methods described above may be applied to any appropriate human or animal anatomy. Methods may be applied to the processing of medical image data obtained using any appropriate type of imaging procedure, for example any appropriate modality, sequence, acquisition type or processing technique. Medical may include veterinary.

Operations described above as being performed on images may in practice be performed on sets of image data that are representative of those images. For example, operations may be performed on data comprising sets of pixel or voxel positions and associated intensities. In many cases, operations are performed on image data without the corresponding images being displayed.

In other embodiments, methods as described above may be performed on any images, which may or may not be medical. In further embodiments, methods as described above may be performed using any suitable data, which may or may not comprise image data. Any suitable primary input, primary output, features and normalizers may be selected. A model may be trained using the features and normalizers such that the model is trained to predict the primary output from the primary input in the absence of the features and normalizers.

Although embodiments above have a primary input that is an image (or image volume), methods described above may also be applied to any suitable type of input, for example any input of high dimensionality. For example, the input may comprise document text. The input may comprise any patient record data.

In some embodiments, the input comprises genomic data. Genomic data input may be presented to the system as raw nucleotide sequences. Genomic data input may be presented to the system as variant calls. Variant calls may comprise summaries of the differences between a subject's genome and a reference genome. The reference genome may also be referred to as a map.

In some embodiments, the input comprises time series data, for example laboratory data or vital signs data.

Whilst particular circuitries have been described herein, in alternative embodiments functionality of one or more of these circuitries can be provided by a single processing resource or other component, or functionality provided by a single circuitry can be provided by two or more processing resources or other components in combination.

Reference to a single circuitry encompasses multiple components providing the functionality of that circuitry, whether or not such components are remote from one another, and reference to multiple circuitries encompasses a single component providing the functionality of those circuitries.

Whilst certain embodiments have been described, these embodiments have been presented by way of example only, and are not intended to limit the scope of the invention. Indeed the novel methods and systems described herein may be embodied in a variety of other forms; furthermore, various omissions, substitutions and changes in the form of the methods and systems described herein may be made without departing from the spirit of the invention. The accompanying claims and their equivalents are intended to cover such forms and modifications as would fall within the scope of the invention.

The invention claimed is:

1. A system comprising processing circuitry configured to perform training of a model for predicting from input data at least one predicted output, wherein to perform training of the model, the processing circuitry is configured to:
receive a plurality of training data sets;
receive from a user a selection of a first characteristic including positive and negative samples each of which is a relevant variation that is significant to prediction of the at least one predicted output;
receive from the user a selection of a second characteristic including an irrelevant sample excluding positive and negative samples and which is a spurious variation that is irrelevant to the prediction of the predicted output;
perform positive supervision of the model using the first characteristic such that the training of the model to predict the at least one predicted output is sensitive to the positive and negative samples of the first characteristic; and
perform negative supervision of the model using the second characteristic such that the training of the model to predict the at least one predicted output is insensitive to the irrelevant sample of the second characteristic.

2. A system according to claim 1, wherein the model comprises a neural network.

3. A system according to claim 1, wherein:
each of the plurality of training data sets comprises respective image data; and
the training of the model further comprises performing supervision of the model using the image data such that the model is trained to use the image data in prediction.

4. A system according to claim 3, wherein the training of the model comprises training the model to predict the at least one predicted output from the image data, such that the trained model is configured to predict the predicted output a target data set in an absence of values for the first characteristic and the second characteristic.

5. A system according to claim 1, wherein the processing circuitry is further configured to receive a target data set and to process the target data set using the trained model to predict said at least one predicted output for the target data set.

6. A system according to claim 1, wherein a first subset of the training data sets comprises training data sets comprising values for the first characteristic, and a second subset of the training data sets comprises training data sets comprising values for the second characteristic.

7. A system according to claim 1, wherein the supervision of the model using the second characteristic is performed using gradient reversal.

8. A system according to claim 1, wherein the first characteristic comprises at least one of: an organ segmentation, an organ volume, a measured shape, a measured texture, a physiological measurement, a data type that is related to a pathology of interest.

9. A system according to claim 1, wherein the first characteristic comprises at least one of a feature extracted from the training data set, a feature computed from the training data set, a manually defined feature, a feature extracted from the input data, a feature computed from the input data.

10. A system according to claim 1, wherein the second characteristic comprises at least one of: scanner manufacturer, acquiring institution, image modality, enumerated protocol variant, image scale, intensity, acquisition direction, presence of image artifacts, a data type that is unrelated to a pathology of interest.

11. A system according to claim 1, wherein the second characteristic comprises at least one of a feature extracted or computed from a training data set, a manually defined feature, a feature extracted from the input data, a feature computed from the input data.

12. A system according to claim 1, wherein the at least one predicted output comprises at least one of: a classification, a regression, a detection, a score, a segmentation.

13. A system according to claim 1, wherein the processing circuitry is further configured to artificially generate further data sets, and wherein the training of the model uses the plurality of training data sets and the generated further data sets.

14. A system according to claim 13, wherein the processing circuitry is configured to artificially generate the further data sets by augmenting at least some of the plurality of training data sets, the augmenting comprising adjusting at least one augmentation parameter of each training data set being augmented and wherein the training of the model comprises performing supervision of the model using the at least one augmentation parameter such that the model is trained to discount values for the at least one augmentation in the prediction of the at least one predicted output.

15. A system according to claim 14, wherein the at least one augmentation parameter comprises at least one of translation, rotation, intensity, contrast, brightness, scale, bias field, flip vertical, flip horizontal.

16. A system according to claim 13, wherein the processing circuitry is configured to artificially generate the further data sets by data synthesis.

17. A system according to claim 1, wherein the input data and training data sets comprise at least one of: document data, text data, genomic data, time series data, laboratory data, vital signs data.

18. A training method to train a model to predict from input data at least one predicted output,
the training method comprising:
receiving a plurality of training data sets;
receiving from a user an identification of a first characteristic of the training data sets, the first characteristic including positive and negative samples each of which is a relevant variation that is significant to prediction of the at least one predicted output;
receiving from the user an identification of a second characteristic of the training data sets, the second characteristic including an irrelevant sample excluding positive and negative samples and which is a spurious variation that is less relevant or irrelevant to prediction of the at least one predicted output; and
training the model, the training of the model comprising:
performing positive supervision of the model using the first characteristic such that training of the model to predict the at least one predicted output is sensitive to the positive and negative samples of the first characteristic; and
performing negative supervision of the model using the second characteristic such that training of the model to predict the at least one predicted output is insensitive to the irrelevant sample of the second characteristic.

19. A system comprising processing circuitry configured to:
receive a target data set; and
process the target data set using a trained model to predict at least one predicted output for the target data set, wherein to train the model, the processing circuitry is configured to:
receive a plurality of training data sets;
receive from a user an identification of a first characteristic of the training data sets, the first characteristic including positive and negative samples each of which is a relevant variation that is significant to prediction of the at least one predicted output;
receive from the user an identification of a second characteristic of the training data sets, the second characteristic including an irrelevant sample excluding positive and negative samples and which is a spurious variation that is less relevant or irrelevant to prediction of the at least one predicted output;

perform positive supervision of the model using the first characteristic such that training of the model to predict the at least one predicted output is sensitive to the positive and negative samples of the first characteristic; and perform negative supervision of the model using the second characteristic such that training of the model to predict the at least one predicted output is insensitive to the irrelevant sample of the second characteristic.

* * * * *